United States Patent [19]

Gervasutti

[11] Patent Number: 4,876,405

[45] Date of Patent: Oct. 24, 1989

[54] PROCESS FOR PREPARING FLUOROETHYLENES AND CHLOROFLUORO-ETHYLENES FROM CHLOROFLUOROETHANES

[75] Inventor: Claudio Gervasutti, Mestre-Venezia, Italy

[73] Assignee: Ausimont S.p.A., Milan, Italy

[21] Appl. No.: 72,641

[22] Filed: Jul. 13, 1987

[30] Foreign Application Priority Data

Jul. 18, 1986 [IT] Italy ................ 21171 A/86

[51] Int. Cl.$^4$ ............... C07C 17/24; C07C 21/18
[52] U.S. Cl. ........................ 570/156; 570/135
[58] Field of Search ................. 570/156, 153

[56] References Cited

U.S. PATENT DOCUMENTS

| | | | |
|---|---|---|---|
| 2,615,925 | 10/1952 | Bordner | 570/156 |
| 2,697,124 | 12/1954 | Mantell | 570/156 |
| 2,704,775 | 3/1955 | Clark | 570/156 |
| 2,704,777 | 3/1955 | Clark | 570/156 |
| 2,734,090 | 2/1956 | Calfee et al. | 570/156 |
| 2,760,997 | 8/1956 | Rucker et al. | 570/156 |
| 2,864,873 | 12/1958 | Miller et al. | 570/156 |
| 3,043,889 | 7/1962 | Smith et al. | 570/156 |
| 3,505,417 | 4/1970 | Gardner | 570/156 |
| 3,636,172 | 1/1972 | Gardner | 570/156 |
| 3,636,173 | 1/1972 | Gardner | 260/653.5 |

FOREIGN PATENT DOCUMENTS

| | | | |
|---|---|---|---|
| 0053657 | 6/1982 | European Pat. Off. | |
| 8454 | 4/1968 | Japan | 570/156 |
| 185734 | 9/1985 | Japan | 570/156 |

*Primary Examiner*—J. E. Evans
*Attorney, Agent, or Firm*—Stevens, Davis, Miller & Mosher

[57] ABSTRACT

A process for preparing fluoroethylenes and chlorofluoroethylenes starting from chlorofluoroethanes and hydrogen, carried out in gas phase at a temperature ranging from 150° to 600° C., in the presence of a hydrogenation catalyst, wherein the chlorofluoroethanes have at least one chlorine atom on each carbon atom, and the catalyst is selected preferably from palladium, nickel, chromium, cobalt, platinum, copper and mixtures thereof, and it is utilized either as such or inert materials.

2 Claims, No Drawings

PROCESS FOR PREPARING FLUOROETHYLENES AND CHLOROFLUORO-ETHYLENES FROM CHLOROFLUOROETHANES

BACKGROUND OF THE INVENTION

1. Field of the Invention

This invention relates to a process for preparing fluoroethylenes and chlorofluoroethylenes by hydrogenolysis of chlorofluoroethanes, comprising also the compounds which contain, besides chlorine and fluorine, one or more hydrogen atoms.

2. The Prior Art

Fluoroethylenes and chlorofluoroethylenes are halogenated olefins well known in literature and they are advantageously utilized as intermediates in the preparation of fluoroplastomers, fluoroelastomers and as comonomers in the preparation of fluorinated copolymers.

Fluorine-containing olefins are generally prepared by dehydrohalogenation or dehalogenation of the corresponding haloalkanes in the liquid phase, according to well known modalities. For example, 1-chloro-1,2-difluoroethylene and 1,2-dichloro-dichloroethylene are prepared by reduction, with zinc in an alcohol solution, of 1,2-difluoro-1,1,2-trichloroethane and 1,2-difluoro-tetrachloroethane, respectively (J. Chem. Soc. London 1957, pages 2800–06). The high addition of zinc necessary to the reaction and its difficult removal render these processes little attractive from an industrial viewpoint.

The preparation of 1,2-difluoroethylene using 1,2-difluoro-tetrachloroethane as a starting material is described in literature. Said reaction occurs in two steps, the former comprising the obtaining of 1,2-difluoro-1,2-dichloroethane through reduction by means of LiAlH$_4$ or through UV-radiations in the presence of 2-propanol, while the latter consists in the dehalogenation of the abovesaid intermediate in the presence of Mg. (Collection Czechloslov. Chem. Commun. Vol. 39, (1974) pages 2801–07).

THE PRESENT INVENTION

It has now surprisingly been found that fluoroethylenes and chlorofluoroethylenes of the above-cited type are preparable in a single step by reaction, in a gas phase, of chlorofluoroethanes with hydrogen, in the presence of hydrogenation catalysts.

Thus, the object of the present invention is a process for preparing fluoroethylenes and chlorofluoroethylenes, comprising reacting hydrogen with chlorofluoroethanes having at least one chlorine atom on each carbon atom, in gas phase, at a temperature ranging from 150° to 600° C. and in the presence of hydrogenation catalysts.

The process of the present invention is an improved as compared with those of the art because of its profitability, easy operability on a commercial scale and because it permits to prepare fluoroethylenes and chlorofluoroethylenes in a single step.

Siad process can be carried out continuously and permits obtaining a very high conversion of the reagents.

Utilizable chlorofluoroethanes of the present invention are the ones, as already mentioned, containing at least one chlorine atom on each carbon atom, in particular 1,2-difluorotetrachloroethane, 1,1-difluorotetrachloroethane, 1,1,2-trichlorotrifluoroethane.

Any hydrogenation catalyst can be used for the process of the present invention; examples thereof are palladium, nickel, chromium, cobalt, platinum, copper, wich can be used either pure or in admixture. In particularly, palladium and nickel are preferred.

Such catalysts can be utilized either as such or, preferably, on inert materials such as, e.g., carbon, aluminium oxide, barium sulphate at concentration ranging from 0.1 to 10% by weight.

Hydrogenation is carried out in tubular reactors made of materials such as, for example, nickel, Inconel, stainless steel.

The hydrogenolysis temperature ranges from 150° C. to 600° C., preferably from 200° C. to 400° C. The process can be carried out either at atmospheric pressure or at a higher pressure.

The contact time of the reagents with the catalyst generally ranges from 5 to 60 seconds, preferably from 10 to 20 seconds.

Hydrogen can be fed either in the pure state or diluted with an inert gas such as for example nitrogen, helium, argon.

The molar ratio between hydrogen and chlorofluoroethanes ranges from 1.0 to 10, preferably from 2 to 5, and it is selected as a function of the product to be obtained; the higher said molar ratio is, the more the product mixture gets rich in hydrogenated fluoroethylenes. Furthermore, when high hydrogen/chlorofluoroethane molar ratios are employed, it is possible also to obtain the saturated products resulting from the addition of hydrogen to the fluoro-olefins and chlorofluoro-olefins produced, such as for example CFHCl—CFHCl, CH$_2$F—CH$_2$F.

According to one preferred embodiment of the present invention, a flow of reagents and hydrogen is continuously fed on the heated catalytic bed.

When leaving the reactor, the vapours are washed with a water solution containing 5-20% by weight of alkaline hydroxide, then they are anhydrified on CaCl$_2$ and cooled until complete condensation.

For a better understanding of the present invention, the following illustrative examples are given, which, however, are not to be construed as a limitation of the invention.

In the examples, the precentages are by weight, unless otherwise specified.

EXAMPLES 1-10

Into a cylindrical reactor made of steel AISI 316, having an inside diameter of 12 mm and a useful volume of 125 cm$^3$, containing 100 cm$^3$ of activated carbon granules with a palladium content of 0.5% by weight, there was introduced, at atmospheric pressure, a mixture, preheated to 105° C., of hydrogen and difluorotetrachloroethane. Difluorotetrachloroethane consisted of a mixture containing 88% by weight of 1,2-difluorotetrachloroethane and 12% by weight of 1,1-difluorotetrachloroethane. Contact time, reaction temperature and H$_2$/C$_2$Cl$_4$F$_2$ molar ratio are indicated in Table 1.

When leaving the reactor, the vapours were washed with a 10% NaOH solution, anhydrified and condensed in a trap maintained at −78° C. means of dry ice.

On gas-chromatographic analysis, the reaction mixture resulted to be composed of:
difluoroethylene (C$_2$H$_2$F$_2$)
chlorodifluoroethylene (C$_2$HClF$_2$)

dichlorodifluoroethylene ($C_2Cl_2F_2$).

The percentages by weight of the products are reported in Table 1.

The balance to 100 consisted of low boiling by-products. Generally, the unreacted starting product was present only in little amounts.

EXAMPLE 11

(comparative test)

The reaction was carried out according to the modalities of Examples 1–10, with a $H_2$/reagents molar ratio equal to 5.0, a contact time of 20 seconds and a temperature of 120° C. The following results (% by weight) were obtained:

| | |
|---|---|
| $C_2H_2F_2$ | 10 |
| $C_2Cl_2F_2$ | 10 |

The balance to hundred consisted of traces of by-products and of unreacted chlorofluroethane (78%).

EXAMPLE 12

Into a cylindrical reactor made of steel AISI 316, having an inside diameter of 12 mm and a useful volume of 125 ml, containing 100 ml of activated carbon granules, with a palladium content of 0.5% by weight, thermoregulated at 320° C., there were introduced, at atmospheric pressure, 0.37 moles/h of a mixture, preheated to 105° C., composed of hydrogen and of 1,1-difluorotetrachloroethane in the following molar ratio: $H_2/C_2Cl_4F_2 = 2.5$.

The vapours leaving the reactor were washed with a NaOH solution at 10%, anhydrified and condensed in a trap maintained at −78° C. by means of dry ice.

On gas-chromatographic analysis, the reaction mixture exhibited the following composition:

| | (% by weight) |
|---|---|
| $CF_2=CCl_2$ | 15.2 |
| $CF_2=CHCl$ | 22.3 |
| $CF_2=CH_2$ | 37.8 |
| $CH_3—CHF_2$ | 9.2 |

EXAMPLE 13

Into the same reactor and under the same conditions as in Example 12 there were introduced, at atmospheric pressure, 0.37 moles/h of a mixture, preheated to 105° C., of hydrogen and of 1,2-difluorotetrachloroethane in a molar ratio $H_2/C_2Cl_4F_2=2.5$.

The vapours leaving the reactor were washed with a 10% NaOH solution, anhydrified and condensed in a trap maintained at −78° C. by means of dry ice. On gas-chromatographic analysis, the reaction mixture exhibited the following composition (% by weight):

| | |
|---|---|
| $CClF=CClF$ | 9.8 |
| $CHF=CHF$ | 53.2 |
| $CClF=CHF$ | 8.4 |
| $CH_2F=CH_2F$ | 8.6 |

The balance to be hundred consisted of low-boiling by-products.

EXAMPLE 14

Into the same reactor and under the same conditions as in Example 12 there was introduced, at atmospheric pressure, a mixture of hydrogen and of 1,1,2-trifluorotrichloroethane in the molar ratio: $H_2/C_2Cl_2F_3=2.4$, said mixture having been preheated to 105° C. The contact time was of 17 seconds. The vapours leaving the reactor were washed with a 10% NaOH solution, anhydrified and condensed in a trap maintained at −78° C. by means of dry ice. The reaction mixture, subjected to gas-chromatographic analysis, exhibited the following composition:

| | (% by weight) |
|---|---|
| $CF_2=CHF$ | 30 |
| $CF_2=CClF$ | 8 |
| $CF_2H—CH_2F$ | 35 |

EXAMPLES 15–17

Under the same conditions as in Example 12, but using as a catalyst Ni on carbon, there was introduced into the usual reactor, at atmosperic pressure, a mixture, preheated to 105° C., composed of hydrogen and of difluorotetrachloroethane (88% by weight of 1,2-difluorotetrachloroethane and 12% by weight of 1,1-difluorotetrachloroethane).

The contact time was of 20 seconds. Three tests were carried out, using different $H_2$/difluorotetrachloroethane molar ratios. The vapours leaving the reactor were treated in like manner as in Example 12.

The gas-chromatographic analysis revealed that the reaction products were present in the % by weight reported in Table 2.

The balance to hundred consisted of low-boiling by-products.

EXAMPLE 18

A test was carried out in the same reactor and under the same operative conditions of Examples 15–17, but using carbon-carried chorome as a catalyst.

The gas-chromatographic analysis revealved that in the product mixture olefin $C_2Cl_2F_2$ was present for 64% by weight.

TABLE 1

| Example | T °C. | Molar ratio | Contact time (sec) | $C_2H_2F_2$ | $C_2HClF_2$ | $C_2Cl_2F_2$ | $C_2H_4F_2$ |
|---|---|---|---|---|---|---|---|
| 1 | 220 | 2.5 | 22 | 51 | 5.2 | 10 | 8.1 |
| 2 | 220 | 3.6 | 20 | 41 | 3.5 | 10 | 24 |
| 3 | 220 | 1.3 | 20 | 13 | 20 | 47 | 2 |
| 4 | 320 | 2.5 | 21 | 55.5 | 6.5 | 13.3 | 6.5 |
| 5 | 320 | 4.2 | 20 | 41 | 5.0 | 5.0 | 25 |
| 6 | 320 | 1.7 | 20 | 11 | 30 | 40.0 | 4.0 |
| 7 | 220 | 5.0 | 20 | 29 | 2.0 | 3 | 43 |
| 8 | 400 | 2.5 | 20 | 61 | 5.0 | 2.2 | 12.3 |
| 9 | 320 | 3.0 | 20 | 51 | 7 | 7 | 11 |

TABLE 1-continued

| Example | T °C. | Molar ratio | Contact time (sec) | $C_2H_2F_2$ | $C_2HClF_2$ | $C_2Cl_2F_2$ | $C_2H_4F_2$ |
| --- | --- | --- | --- | --- | --- | --- | --- |
| 10 | 150 | 2.5 | 20 | 15 | 10 | 32 | 3.5 |

TABLE 2

| Example | Molar ratio | $C_2H_2F_2$ | $C_2HClF_2$ | $C_2Cl_2F_2$ | $C_2H_2Cl_2F_2$ |
| --- | --- | --- | --- | --- | --- |
| 15 | 5.0 | 80 | — | — | 7 |
| 16 | 2.5 | 45 | 37 | — | 1.5 |
| 17 | 1.3 | 5 | 24 | 62 | 1.2 |

What I claim is:

1. A process for the selective dehalogenation of chlorofluoroethanes selected from the group consisting of 1,2-difluoro-tetrachloroethane and 1,1-difluorotetrachloroethane and mixtures thereof in gas phase to fluoroethylenes and chlorofluoroethylenes containing at least one hydrogen atom, comprising reacting hydrogen in one step with the chlorofluoroethanes at a temperature ranging from 200° C. to 400° C. with a molar ratio of hydrogen to the chlorofluoroethane ranging from 2 to 5, in the presence of a hydrogenation catalyst selected from palladium and nickel.

2. A process for the selective dehalogenation of chlorofluoroethanes selected from the group consisting of 1,2-difluoro-tetra-chloroethane and 1,1-difluorotetra chloroethane and mixtures thereof in gas phase, to fluoroethylenes and chlorofluoroethylenes containing at least one hydrogen atoms, comprising reacting in one step hydrogen with the chlorofluoroethanes at a temperature ranging from 200° C. to 400° C. with a molar ratio of hydrogen to the chlorofluoroethane ranging from 2 to 5, in the presence of a hydrogenation catalyst selected from palladium and nickel, supported on active carbon.

* * * * *